(12) United States Patent
Hafner et al.

(10) Patent No.: US 8,716,305 B2
(45) Date of Patent: May 6, 2014

(54) MULTICOMPONENT CRYSTALLINE SYSTEM OF ROSUVASTATIN CALCIUM SALT AND VANILLIN

(75) Inventors: Andreas Hafner, Gelterkinden (CH); Fritz Blatter, Reinach (CH); Martin Szelagiewicz, Basel (CH); Bernd Siebenhaar, Kandern-Wollbach (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/643,579

(22) PCT Filed: Apr. 16, 2012

(86) PCT No.: PCT/EP2012/056863
§ 371 (c)(1),
(2), (4) Date: Dec. 17, 2012

(87) PCT Pub. No.: WO2012/143308
PCT Pub. Date: Oct. 26, 2012

(65) Prior Publication Data
US 2014/0031377 A1    Jan. 30, 2014

Related U.S. Application Data

(60) Provisional application No. 61/476,334, filed on Apr. 18, 2011.

(30) Foreign Application Priority Data

Apr. 18, 2011    (EP) .................................... 11162801

(51) Int. Cl.
*A01N 43/42* (2006.01)
*A61K 31/44* (2006.01)
*A61K 31/505* (2006.01)
*C07D 239/42* (2006.01)

(52) U.S. Cl.
CPC ............ *A61K 31/505* (2013.01); *C07D 239/42* (2013.01)
USPC .......................................... 514/275; 544/297

(58) Field of Classification Search
CPC ............................ C07D 239/42; A61K 31/505
USPC .......................................... 544/297; 514/275
See application file for complete search history.

(56) References Cited

U.S. PATENT DOCUMENTS

| 5,260,440 | A  | * | 11/1993 | Hirai et al. ..................... 544/332 |
| 6,589,959 | B1 |   | 7/2003  | Taylor |
| 7,932,387 | B2 | * | 4/2011  | Blatter et al. ................. 544/332 |
| 2005/0080134 | A1 | | 4/2005 | Niddam-Hildesheim et al. |
| 2005/0131066 | A1 | | 6/2005 | Niddam-Hildesheim et al. |
| 2005/0159615 | A1 | | 7/2005 | Lifshitz-Liron et al. |
| 2006/0089501 | A1 | | 4/2006 | Niddam-Hildesheim et al. |
| 2007/0099994 | A1 | | 5/2007 | Niddam-Hildesheim et al. |
| 2007/0105881 | A1 | * | 5/2007 | Hendrix et al. ............... 514/269 |
| 2007/0123550 | A1 | | 5/2007 | Niddam-Hildesheim et al. |
| 2007/0167625 | A1 | | 7/2007 | Balanov et al. |
| 2008/0176878 | A1 | | 7/2008 | Wizel et al. |
| 2008/0194604 | A1 | * | 8/2008 | Blatter et al. ................. 514/275 |

FOREIGN PATENT DOCUMENTS

| EP | 1 663 989 A1 | 6/2006 |
| WO | WO 00/42024 A1 | 7/2000 |
| WO | WO 2005/023779 A1 | 3/2005 |
| WO | WO 2006/079611 A1 | 8/2006 |
| WO | WO 2008/036286 A1 | 3/2008 |
| WO | WO 2008/069546 A1 | 6/2008 |
| WO | WO 2012/069394 A1 | 5/2012 |
| WO | WO 2012/124973 A2 | 9/2012 |

OTHER PUBLICATIONS

S.L. Morissette et al., Advanced Drug Delivery Reviews, 56, 275-300 (2004).*
S.R. Vippagunta et al., Advanced Drug Delivery Reviews, 48, 3-26 (2001).*
J.K. Guillory, Generation of Polymorphs, Hydrates, Solvates, and Amorphous Solids, in Polymorphism in Pharmaceutical Solids 183-220 (H.G. Brittain ed., 1999).*
H.G. Brittain, Preparation and Identification of Polymorphs and Solvatomorphs in, Preformulation in Solid Dosage Form Development, 185-228 (5th ed., M. C. Adeyeye et al., eds., 2008).*
U.S. Appl. No. 13/574,005, filed Jul. 19, 2012, Hafner, et al.
International Search Report issued May 18, 2012 in PCT/EP2012/056863 filed Apr. 16, 2012.
German Search Report Issued Jul. 8, 2013 in Patent Application No. 20 2012 011 888.9.

* cited by examiner

*Primary Examiner* — Deepak Rao
*Assistant Examiner* — Alexander R Pagano
(74) *Attorney, Agent, or Firm* — Oblon, Spivak, McClelland, Maier & Neustadt, L.L.P.

(57) ABSTRACT

A novel solid form of Rosuvastatin comprises as the active ingredient a salt of bis[(E)-7-[4-(4-fluorophenyl)-6-isopropyl-2-[methyl(methylsulfonyl)-amino]pyrimidin-5-yl]-(3R,5S)-3,5-dihydroxyhept-6-enoic acid] and vanillin or vanillin derivatives. The crystal comprising the two components, and minor amounts of water, shows improved properties such as crystallization behavior stability and decreased hydroscopic behavior.

10 Claims, 1 Drawing Sheet

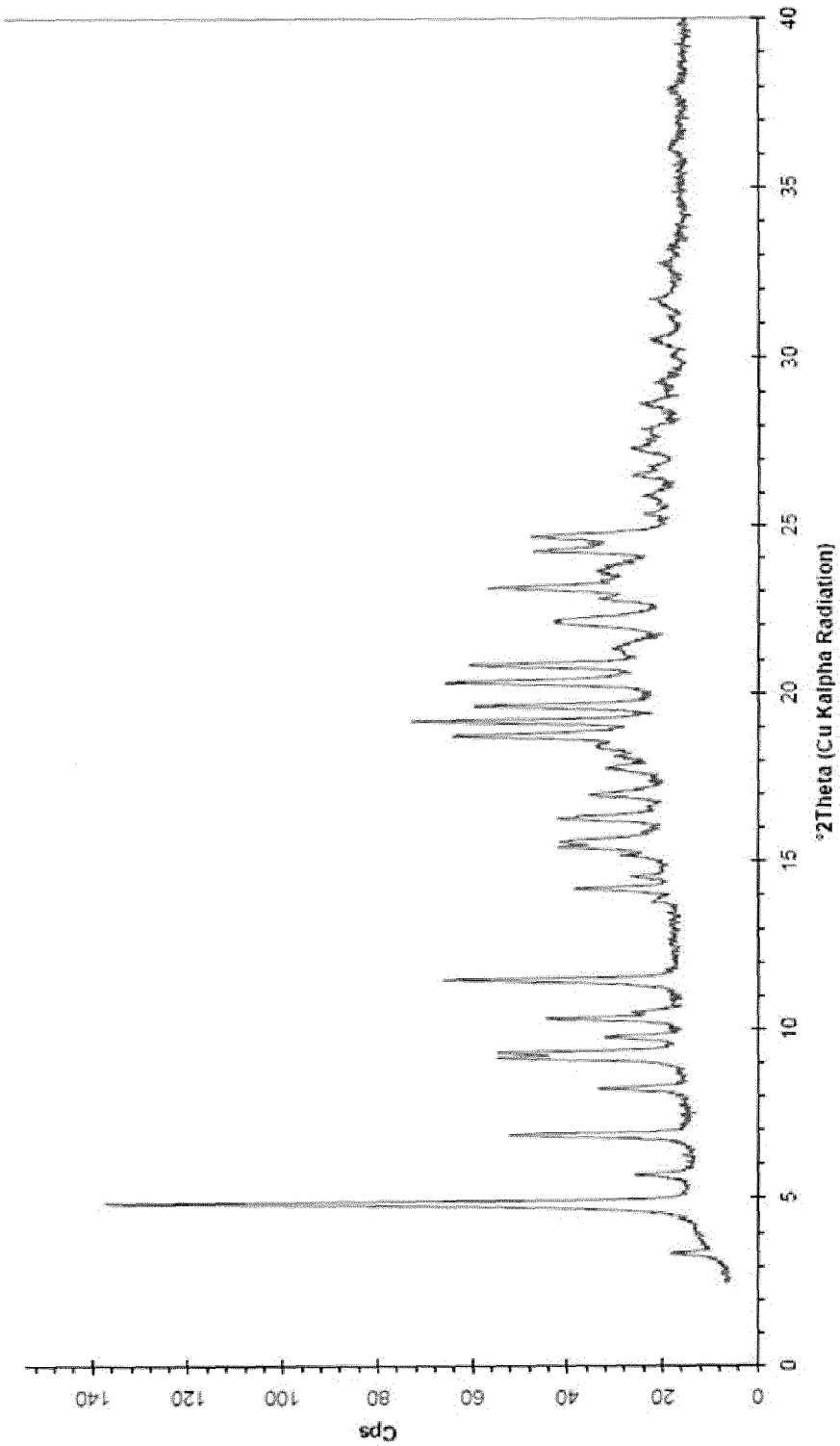

MULTICOMPONENT CRYSTALLINE SYSTEM OF ROSUVASTATIN CALCIUM SALT AND VANILLIN

The present invention relates to a multicomponent system comprising rosuvastatin calcium salt and vanillin or vanillic acid to pharmaceutical preparations comprising said system, and specifically to a homogenous crystalline phase (cocrystal) comprising rosuvastatin calcium and vanillin. The invention also relates to processes for preparing said multicomponent system and crystalline phase. The invention also relates to compositions comprising said multicomponent system or crystalline phase and a pharmaceutically acceptable carrier, and to methods of using said multicomponent system or crystalline phase to treat a disease condition wherein inhibition of HMG CoA reductase is beneficial.

Rosuvastatin calcium is known as the calcium salt of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid], specifically the calcium salt of formula (1)

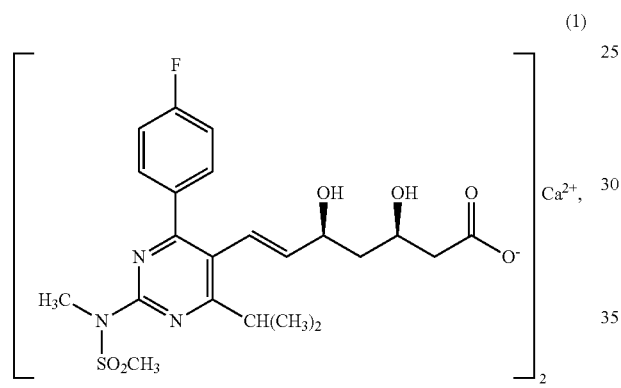

(1)

It is known to inhibit the HMG-CoA reductase, and subsequently suppress the biosynthesis of cholesterol. The compound is also known as Rosuvastatin hemicalcium salt, corresponding to half of the molecular weight shown in the above formula (1). Rosuvastatin calcium is useful in the treatment of hypercholesterolemia, hyperlipoproteinemia, and atherosclerosis. Rosuvastatin calcium may form hydrates with a varying content of water.

In WO 00/42024 is disclosed a crystalline form, hereafter referred to as form A of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof, which are prepared by dissolving the amorphous form in a mixture of water and an organic solvent such as acetone or acetonitrile under heating and then cooling the solution to precipitate crystalline form A.

WO 06/079611 discloses some further crystalline forms of rosuvastatin calcium including form B. Further documents disclosing certain crystalline forms of rosuvastatin calcium are EP-A-1663989 and US-A-2008-176878.

Existing solid forms of rosuvastatin calcium still leave room for improvement of physical as well as biological characteristics. There exists a need for other solid forms, especially crystalline forms, of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt for sufficient diversity on crystalline materials to optimize manufacture, formulation and biological efficiency.

SUMMARY OF THE INVENTION

The invention provides a novel solid form of rosuvastatin calcium characterized by a content of vanillin or vanillin derivatives and, consequently, novel pharmaceutical formulations containing this form. The invention further provides a novel crystalline form of rosuvastatin calcium, and processes for manufacture thereof.

Crystalline forms often show desired different physical and/or biological characteristics which may assist in the manufacture or formulation of the active compound, to the purity levels and uniformity required for regulatory approval. The present solid form, especially crystalline form, may possess improved pharmacological characteristics, for example, improved bioavailability, thus offering enhanced possibilities to modulate and design improved drug products.

DETAILED DESCRIPTION OF THE INVENTION

The solid form of the invention is a composite comprising two components, which are a rosuvastatin salt, especially rosuvastatin calcium, and vanillin or vanillin derivatives like vanillic acid, acetovanillon, isovanillin, ethylvanillin, or ortho-vanillin within one single phase:

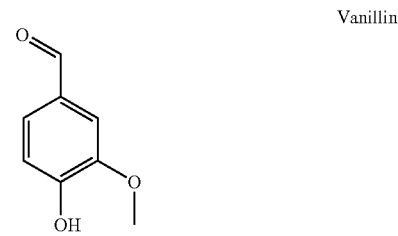

Vanillin

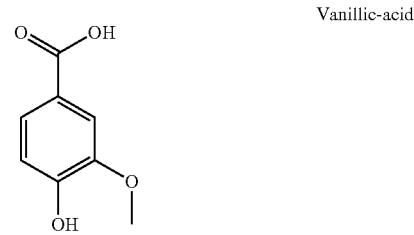

Vanillic-acid

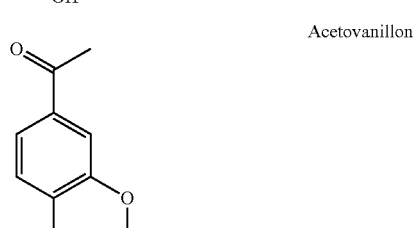

Acetovanillon

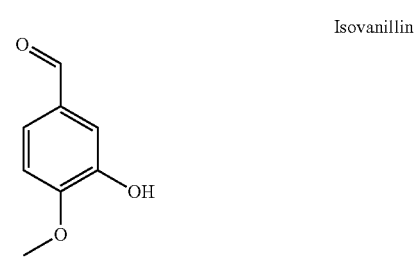

Isovanillin

-continued

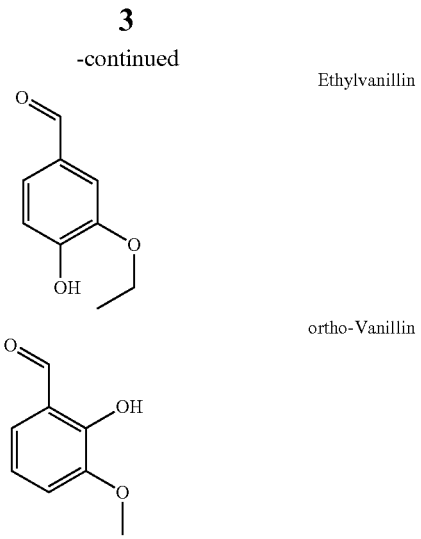

Ethylvanillin ortho-Vanillin

More specifically, the invention provides a multicomponent molecular crystal (i.e. a co-crystal) containing a salt of Rosuvastatin and vanillin, preferably the hemi Ca salt of bis[(E)-7-[4-(4-fluorophenyl)-6-isopropyl-2-[methyl(methylsulfonyl)-amino]pyrimidin-5-yl](3R,5S)-3,5-dihydroxyhept-6-enoic acid] and vanillin or vanillic-acid, acetovanillon, isovanillin, ethylvanillin, or ortho-vanillin The solid phase generally contains 0.1 to 1.5 molar parts of vanillin or vanillic-acid, acetovanillon, isovanillin, ethylvanillin, or ortho-vanillin, on 1 molar unit of [(E)-7-[4-(4-fluorophenyl)-6-isopropyl-2-[methyl(methylsulfonyl)-amino]pyrimidin-5-yl](3R,5S)-3,5-dihydroxyhept-6-enoic acid].

More specifically, the solid phase contains 0.4 to 0.6 molar parts, of vanillin on 1 molar unit [(E)-7-[4-(4-fluorophenyl)-6-isopropyl-2-[methyl(methylsulfonyl)-amino]pyrimidin-5-yl](3R,5S)-3,5-dihydroxyhept-6-enoic acid]. The salt is preferably the calcium or sodium salt, especially the hemi calcium salt. Preferred are is a ratio of about 0.5:1 (i.e. 1:2 adduct).

The invention thus includes
i) a multicomponent molecule crystal containing a salt of bis[(E)-7-[4-(4-fluorophenyl)-6-isopropyl-2-[methyl(methylsulfonyl)-amino]pyrimidin-5-yl](3R,5S)-3,5-dihydroxyhept-6-enoic acid] and of vanillin or vanillic-acid or acetovanillon or isovanillin or ethylvanillin, or ortho-vanillin
ii) a multicomponent molecular crystal containing a hemi Ca salt of bis[(E)-7-[4-(4-fluorophenyl)-6-isopropyl-2-[methyl (methylsulfonyl)-amino]pyrimidin-5-yl](3R,5S)-3,5-dihydroxyhept-6-enoic acid] and vanillin or vanillic-acid or acetovanillon or isovanillin or ethylvanillin, or ortho-vanillin;
iii) a multicomponent molecular crystal containing 0.1 to 1.5 molar parts, preferably 0.3 to 1.1 molar parts, and much preferred 0.4 to 0.6 molar parts, Vanillin or vanillic-acid or acetovanillon or isovanillin or ethylvanillin, or ortho-vanillin; on 1 molar part of bis[(E)-7-[4-(4-fluorophenyl)-6-isopropyl-2-[methyl(methylsulfonyl)-amino]pyrimidin-5-yl](3R,5S)-3,5-dihydroxyhept-6-enoic acid] as calcium and preferably as hemi calcium salt;
iv) a solid form as defined under i-iii consisting essentially of bis[(E)-7-[4-(4-fluorophenyl)-6-isopropyl-2-[methyl(methylsulfonyl)-amino]pyrimidin-5-yl](3R,5S)-3,5-dihydroxyhept-6-enoic acid] calcium salt, vanillin or vanillic-acid or acetovanillon or Isovanillin or ethylvanillin or ortho-vanillin as minor component by weight.
v) Preferred is a solid form as defined under i-iv consisting essentially of bis[(E)-7-[4-(4-fluorophenyl)-6-isopropyl-2-[methyl(methylsulfonyl)-amino]pyrimidin-5-yl](3R,5S)-3, 5-dihydroxyhept-6-enoic acid] calcium salt and vanillin as a component.

Preferred solid form may be further characterized by its high crystallinity and/or high melting point of above 100° C. (m.p. e.g. from the range 100-120° C., especially from the range 102-110° C.) and high melting enthalpy Δ H>40 J/g (see present examples). While showing a good solubility, the present solid form provides better stability, and provides advantages in processing due to its good crystallization properties (crystallisation from water without co solvents).

Vanillin and rosuvastatin are present in the same solid phase, preferably in the same crystalline phase, i.e. forming a co-crystal; hereinafter designated as form E. The invention thus further pertains to a novel crystalline form of rosuvastatin calcium, which crystalline form is characterized by containing vanillin within its crystalline structure, e.g. in amounts as indicated above. A preferred novel crystalline form generally exhibits a characteristic X-ray powder diffraction pattern with characteristic peaks expressed in d-values (Å) 25.4 (vw). 18.0 (S) 9.5 (s) 7.7 (s), 4.73 (s), 4.62 (vs), 4.52 (s), 4.36 (vs), 4.26 (vs), 4.01 (s), 3.84 (s), 3.66 (s), 3.60 (vs).

More specifically, the present invention comprises a crystalline form of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof, which exhibits a characteristic X-ray powder diffraction pattern with characteristic peaks expressed in d-values (Å) as shown in the below table:

| d-spacing [Å] | Rel. Int. qualitatively |
| --- | --- |
| 25.4 | vw |
| 18.0 | vs |
| 15.4 | vw |
| 12.8 | m |
| 10.7 | w |
| 9.5 | s |
| 9.0 | w |
| 8.5 | m |
| 7.7 | s |
| 6.2 | w |
| 5.73 | m |
| 5.65 | m |
| 5.43 | m |
| 5.20 | w |
| 4.97 | w |
| 4.73 | s |
| 4.62 | vs |
| 4.52 | s |
| 4.36 | vs |
| 4.26 | vs |
| 4.01 | s |
| 3.84 | s |
| 3.66 | s |
| 3.60 | vs |
| 3.43 | vw |
| 3.35 | vw |
| 3.27 | w |
| 3.20 | w |
| 3.11 | w |
| 3.05 | vw |
| 2.93 | w |
| 2.82 | w |

Here and in the following the abbreviations in brackets mean: (vs)=very strong intensity; (s)=strong intensity; (m)=medium intensity; (w)=weak intensity. (vw)=very-weak, intensity In still another preferred embodiment, the present invention comprises a crystalline form D of bis[(E)-7-[4-(4-fluorophenyl)-6-isopropyl-2-[methyl(methylsulfonyl)amino]-pyrimidin-5-yl](3R,5S)-3,5-dihydroxyhept-6-enoic acid] calcium salt and hydrates thereof, which exhibits characteristic X-ray powder diffraction patterns as exhibited in FIG. 1.

Another object of the invention is a process for the preparation of crystalline form E of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt (Rosuvastatin calcium) and hydrates thereof which comprises the steps of a) providing vanillin, or a suitable derivative thereof (vanillic acid or isovanillin or ortho-vanillin or ethylvanillin or acetovanillon), b) providing a solution of Rosuvastatin calcium (e.g. crude Rosuvastatin calcium or another form of Rosuvastatin in combination with an equivalent or excess amount of calcium, e.g. from synthesis) in a suitable solvent, c) combining the solutions or suspension provided in steps (a) and (b), and d) separating the precipitate and drying.

Step (a) usually comprises providing vanillin in solid form, or as a solution of vanillin in water, or water containing minor amounts of a water miscible solvent as defined for (b) below.

The solvent used in step (b) is water or a water miscible organic solvent such as an alcohol (e.g. methanol, ethanol, propanol, butanol), or an ester (such as ethyl acetate, methyl acetate), ethers such as methyl-tert.butylether, or an aliphatic ketone (e.g. acetone, methyl ethyl ketone), or mixture of such solvents, or such a solvent with water. Solutions or suspension according to steps (a) and (b) preferably are concentrated solutions.

The concentration of rosuvastatin calcium may range from 0.1 to about 300 mg/ml of solvents (including water), preferably from 5 to 200 mg/ml.

The process is preferably carried out in the temperature range 15-50° C., for example at ambient temperature. In a preferred process, step (c) is carried out at a temperature from the range 20-60° C. or the mixture is heated to a temperature from said range, e.g. about 50° C. The suspension thus tempered is then preferably cooled before step (d). In a preferred process, the step is accompanied by seeding with crystals of form E (e.g. 1-10% b.w. of the total amount of rosuvastatin) at a temperature of about 20-50° C.

Ambient temperature means in the context of the invention a temperature range at room temperature, comprising 20 to 30° C. and preferably about 20 to 25° C.

As an alternative, the present solid form may be prepared by melt-extruding a suitable mixture of the Rosuvastatin salt and the vanillin component (vanillin or vanillic acid or isovanillin or ortho-vanillin or ethylvanillin or acetovanillon).

Crystal form E is isolated by filtering off the crystals and drying, e.g. in vacuum, an inert gas flow or both at ambient temperature, or elevated temperatures up to 60° C.

Form E is thermodynamically stable and can be dried at elevated temperatures, e.g. below 80° C., and is obtained as a fine powder with typical particle size distributions with the median size between 1 and 50 µm, preferably between 1 to 10 µm. This particle size range ensures a fast dissolution profile, while retaining the favorable handling properties in the formulation process.

Form E is less prone to water uptake under humidity, and is easy to formulate compared to Crystal form A.

| | Crystal form A [1] | Crystal form E [2] |
|---|---|---|
| Water vapor sorption: water content after 2 h at 50% r.h. | 6.2% | 2.6% |
| Water vapor sorption: water content after 5 h at 95% r.h. | 10.1% | 5.0% |

Present Form E generally contains minor amounts of water, mainly within its crystal structure, the amounts usually ranging from 1.5 to 5% of water, relative to the total weight of the solid phase, especially of the crystalline form E The solid form E may be used in pharmaceutical compositions in the same way as other forms of Rosuvastatin calcium previously known. Additionally, present form E based on any pharmaceutically acceptable salt of rosuvastatin, such as sodium or calcium salt, may be employed as an intermediate or starting material to produce the pure active ingredient, e.g. in form of crystal form A.

The present invention is also directed to a pharmaceutical composition comprising a solid form containing vanillin, or especially crystal form E, of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof, and a pharmaceutically acceptable carrier or diluent.

The amount of solid (especially crystalline) forms of bis [(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof substantially depends on type of formulation and desired dosages during administration time periods. The amount in an oral formulation may be from 0.1 to 200 mg, preferably from 0.5 to 100 mg, and more preferably from 1 to 50 mg.

Oral formulations may be solid formulations such as capsules, tablets, pills and troches, or liquid formulations such as aqueous suspensions, elixirs and syrups. Solid and liquid formulations encompass also incorporation of the present solid form, especially crystal form E, into liquid or solid food.

The solid forms according to the invention may be directly used as powders (micronized particles), granules, suspensions or solutions, or they may be combined together with other pharmaceutically acceptable ingredients in admixing the components and optionally finely divide them, and then filling capsules, composed for example from hard or soft gelatine, compressing tablets, pills or troches, or suspend or dissolve them in carriers for suspensions, elixirs and syrups. Coatings may be applied after compression to form pills.

Pharmaceutically acceptable ingredients are well known for the various types of formulation and may be for example binders such as natural or synthetic polymers, excipients, lubricants, surfactants, sweetening and other flavouring agents, coating materials, preservatives, dyes, thickeners, adjuvants, antimicrobial agents and carriers for the various formulation types.

Examples for binders are gum tragacanth, acacia, starch, gelatine, and biological degradable polymers such as homo- or co-polyesters of dicarboxylic acids, alkylene glycols, polyalkylene glycols and/or aliphatic hydroxyl carboxylic acids; homo- or co-polyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers may be linear, branched or crosslinked. Specific examples are poly-glycolic acid, poly-lactic acid, and poly-d,l-lactide/glycolide. Other examples for polymers are water-soluble polymers such as polyoxaalkylenes (polyoxaethylene, polyoxapropylene and mixed polymers thereof, poly-acrylamides and hydroxylalkylated polyacrylamides, poly-maleic acid and esters or -amides thereof, poly-acrylic acid and esters or -amides thereof, poly-vinylalcohol und esters or -ethers thereof, poly-vinylimidazole, poly-vinylpyrrolidon, und natural polymers like chitosan, carragenan or hyaluronic aid.

Examples for excipients are phosphates such as dicalcium phosphate.

Examples for lubricants are natural or synthetic oils, fats, waxes, or fatty acid salts like magnesium stearate.

Surfactants may be anionic, anionic, amphoteric or neutral. Examples for surfactants are lecithin, phospholipids, octyl sulfate, decyl sulfate, dodecyl sulfate, tetradecyl sulfate, hexadecyl sulfate and octadecyl sulfate, Na oleate or Na caprate, 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or -distearate, glycerol mono- or -dioleate and glycerol mono- or -dipalmitate, and polyoxyethylene stearate.

Examples for sweetening agents are sucrose, fructose, lactose or aspartam.

Examples for flavouring agents are peppermint, oil of wintergreen or fruit flavours like cherry or orange flavour.

Examples for coating materials gelatine, wax, shellac, sugar or biological degradable polymers.

Examples for preservatives are methyl or propylparabens, sorbic acid, chlorobutanol, phenol and thimerosal.

Examples for adjuvants are fragrances.

Examples for thickeners are synthetic polymers, fatty acids and fatty acid salts and esters and fatty alcohols.

Examples for liquid carriers are water, alcohols such as ethanol, glycerol, propylene glycol, liquid polyethylene glycols, triacetin and oils. Examples for solid carriers are talc, clay, microcrystalline cellulose, silica, alumina and the like.

The formulation according to the invention may also contain isotonic agents, such as sugars, buffers or sodium chloride.

The solid forms according to the invention may also be formulated as effervescent tablet or powder, which disintegrate in an aqueous environment to provide a drinking solution.

A syrup or elixir may contain the cocrystal of the invention, sucrose or fructose as sweetening agent a preservative like methylparaben, a dye and a flavouring agent.

The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages may be conveniently presented in unit dosage form and prepared by any of the methods well-known in the art of pharmacy.

Dosage forms include solid dosage forms, like tablets, powders, capsules, suppositories, sachets, troches and losenges as well as liquid suspensions and elixirs. While the description is not intended to be limiting, the invention is also not intended to pertain to true solutions of Rosuvastatin calcium whereupon the properties that distinguish the solid forms of Rosuvastatin calcium are lost. However, the use of the novel forms to prepare such solutions is considered to be within the contemplation of the invention.

Capsule dosages, of course, will contain the solid composition within a capsule which may be made of gelatin or other conventional encapsulating material. Tablets and powders may be coated. Tablets and powders may be coated with an enteric coating. The enteric coated powder forms may have coatings comprising phthalic acid cellulose acetate, hydroxypropylmethyl-cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

Slow release formulations may also be prepared from the crystal form according to the invention in order to achieve a controlled release of the active agent in contact with the body fluids in the gastro intestinal tract, and to provide a substantial constant and effective level of the active agent in the blood plasma. The crystal forms may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

The crystal forms of the invention are also useful for administering a combination of therapeutic effective agents to an animal. Such a combination therapy can be carried out in using at least one further therapeutic agent which can be additionally dispersed or dissolved in a formulation.

The crystal forms of this invention and its formulations respectively can be also administered in combination with other therapeutic agents that are effective to treat a given condition to provide a combination therapy.

The crystal forms and the pharmaceutical composition according to the invention are highly suitable for effective treatment of disorders in connection with need of inhibiting the HMG-CoA reductase, and subsequently suppressing the biosynthesis of cholesterol. Crystalline forms of this invention and pharmaceutical composition are useful in the treatment of hypercholesterolemia, hyperlipoproteinemia, and atherosclerosis.

An object of the invention is also a therapeutic method for producing an HMG-CoA reductase inhibiting effect in a mammal comprising administering to a mammal in need of such therapy, an effective amount of the present composite containing vanillin, especially crystal form E, of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt, and hydrates thereof.

The multicomponent crystal of the invention may be used as single component or as mixtures with other solid forms, which may be crystalline or amorphous.

As to the novel multicomponent crystal of Rosuvastatin calcium it is preferred that these contain 25-100% by weight, especially 50-100% by weight, based on the total amount of Rosuvastatin calcium. Preferably, such an amount of the novel multicomponent crystal forms of Rosuvastatin calcium is 75-100% by weight, especially 90-100% by weight. Highly preferred is an amount of 95-100% by weight.

Another object of the invention is a method of delivering a solid form of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and/or hydrates thereof to a host, which method comprises administering to a host an effective amount of said solid form, especially crystal form E, according to the invention.

A further object of the invention is the use of a crystal form D and/or solid form containing vanillin, of bis[(E)-7-[4-(4-fluorophenyl)-6-isopropyl-2-[methyl(methylsulfonyl) amino]pyrimidin-5-yl](3R,5S)-3,5-dihydroxyhept-6-enoic acid] calcium salt, and hydrates thereof, for the manufacture of a medicament useful in the treatment of disorders in connection with need of inhibiting the HMG-CoA reductase, and subsequently suppressing the biosynthesis of cholesterol, and especially useful in the treatment of hypercholesterolemia, hyperlipoproteinemia, and atherosclerosisin in a mammal, such as a human; and the solid forms according to the invention for use in medical therapy.

The following examples illustrate the invention.

Wherever noted, room temperature depicts a temperature from the range 20-25° C.; percentages are given by weight, if not indicated otherwise.

Abbreviations:

| | |
|---|---|
| DMSO | dimethyl sulfoxide |
| HPLC | high pressure liquid chromatography |
| NMR | nuclear magnetic resonance |
| FTIR | Fourier-transformation infrared spectrometry |
| r.h. | relative humidity (air, if not indicated otherwise) |
| TG | thermogravimetry |
| DSC | differential scanning calorimetry |
| v/v | volume by volume |
| PXRD | Powder X-ray diffraction |

Instrumental

PXRD is carried out with a Bruker D8 Advance powder X-ray diffractometer using $Cu_{K-alpha}$ radiation in reflection (Bragg-Brenatno) geometry. 2θ values are accurate within an error of ±0.1-0.2°. The samples are prepared without any special treatment other than the application of slight pressure to get a flat surface. About 3-5 mg of the sample are placed on a 0.1 mm depth standard silicon single crystal sample holder. The tube volt-age is 40 kV and current was 40 mA. The PXRD diffractometer is equipped with a LynxEye detector. A variable divergence slight is used with a 3° window. The step size is 0.02° 2θ with a step time of 37 seconds. The samples are rotated at 0.5 rps during the measurement.

Thermogravimetry coupled to infrared spectroscopy (TG-FTIR):

The thermo gravimetric measurements are carried out with a Netzsch Thermo-Microbalance TG 209 coupled to a Bruker FTIR Spectrometer IFS 28 or Vector 22 (sample pan with a pinhole, N2 atmosphere, heating rate 10 K/min, range 25° C. to 250° C.).

DSC:

Differential scanning calorimetry is carried out with a Perkin Elmer DSC7 using hermetically closed gold sample pans. Heating rate: 10K/minute.

1H-NMR:

The 1H-NMR spectra are recorded on a Bruker DPX 300 spectrometer.
Solvent: DMSO-d6.

EXPERIMENTAL

Solvents: For all experiments, Fluka or Sigma Aldrich grade solvents are used. Selected solvents are dried using 3 or 4 Å molecular sieves.

Crystallization Experiments

The crystallization experiments are performed in Supelco glass vials using magnetic stirrers.

Aqueous Solubility Determination

Approximately 0.5 mL of doubly distilled water is added to 10 to 40 mg of the sub-stance to be measured. The resulting suspension is equilibrated in a temperature-controlled Eppendorf Thermomixer Comfort shaker for 2 h and 24 h at 25° C. at a shaking rate of 400 rpm. After 24 h the solid phase is recovered by filter centrifugation (0.10-μm PVDF membrane) and examined by XRPD. Concentrations in the filtrate after 2 h and 24 h (i.e., saturated solutions) are determined using HPLC. The pH of the saturated solution is determined with a Metrohm 713 pH meter.

Example 1

Preparation of Cocrystal with Vanillin (Form E) (Seeding Material)

125 mg of amorphous or mesomorphic Rosuvastatin hemicalcium salt and 38 mg of vanillin are suspended in 10 mL of water at room temperature. The system is sonicated for 1 minute and stirred for 4 days at room temperature and sonicated once per day. The suspension formed is filtered, air dried for 10 minutes and further dried at 50° C./30 mbar for 2 hours. The yield is 76 mg (approx. 53%). XRPD shows the pattern of crystal form E, and TG-FTIR shows a mass loss of 1.7% (water; 25° C. to 150° C.). 1H-NMR (measured in DMSO-d6) shows the spectrum of a mixture of Rosuvastatin hemicalcium salt and vanillin (molar ratio Rosuvastatin hemicalcium salt:vanillin 1:0.6). DSC in a closed sample pan shows an endothermal effect with a peak temperature of 103.2° C. (65 J/g).

Example 2

Preparation of Co-Crystal with Vanillin (Form E)

502 mg of amorphous or mesomorphic Rosuvastatin hemicalcium salt are suspended in 20 mL of a saturated solution of vanillin in water at room temperature. The suspension is seeded with approx. 10 mg of the Rosuvastatin hemicalcium salt vanillin co-crystal (product of example 1), heated to 50° C. and stirred for 1 hour at 50° C. The suspension is cooled to room temperature and stirred for 16 hours at room temperature. To the easily stirrable suspension, 10 mL of water are added and the suspension is stirred for an additional 1.5 hours.

The suspension is filtered, washed two times with 5 mL of water, air dried for 10 minutes and further dried at 50° C./30 mbar for 2 hours. The yield is 481 mg (approximately 83%). XRPD shows the pattern of crystal form E, and TG-FTIR shows a mass loss of 1.6% (water; 25° C. to 150° C.). $^1$H-NMR (measured in DMSO-d6) shows the spectrum of a mixture of Rosuvastatin hemicalcium salt and vanillin (molar ratio Rosuvastatin hemicalcium salt:vanillin 1:0.5). DSC in a closed sample pan shows an endothermal effect with a peak temperature of 107.7° C. (62 J/g)

Example 3

Characterization of Co-Crystal

In order to further investigate the product obtained in examples 1 and 2, some additional experiments and characterizations are carried out:
(a) z.B. 1H-NMR spectroscopy shows that crystal form E according to example 1 contains Rosuvastatin and Vanillin at a molar ratio of 1:0.6, and that crystal form E according to example 2 contains Rosuvastatine and Vanillin at a molar ratio of 1:0.5
(b) The DSC diagram does not indicate the presence of any of the crystal forms of vanillin given in publication Svärd-2007 (Journal of Pharmaceutical Sciences 96, 2007, 2390-2398) or the amorphous form. The melting peak does not indicate eutectic impurities. The melting peak temperature of both samples is well above the melting temperatures of the known crystal forms of vanillin.

BRIEF DESCRIPTION OF FIGURES

FIG. 1: Powder X-Ray Diffraction pattern of Rosuvastatin hemicalcium salt/crystal form E (1:0.5 co-crystal with vanillin)

The invention claimed is:

1. A cocrystal of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt with vanillin, or a hydrate thereof, exhibiting an X-ray powder diffraction pattern with characteristic peaks expressed in d-values (A) of: 25.4 (vw), 18.0 (s), 9.5 (s), 7.7 (s), 4.73 (s), 4.62 (vs), 4.52 (s), 4.36 (vs), 4.26 (vs), 4.01 (s), 3.84 (s), 3.66 (s), and 3.60 (vs).

2. The cocrystal of claim 1, which is characterized by a melting peak temperature greater than 90° C. and an enthalpy of fusion greater than 40 Joule per gram when 2.5 to 4.0 mg of a sample of the cocrystal is measured in a gold sample pan hermetically sealed at a relative humidity of 25+/−10%.

3. A cocrystal of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt with vanillin, or a hydrate thereof, exhibiting an X-ray powder diffraction pattern essentially as exhibited in FIG. 1.

4. A process for the preparation and/or purification of the cocrystal of claim 1, the process comprising:
 a) providing a solution or suspension of vanillin in water,
 b) adding Rosuvastatin calcium salt to the solution as solid or as suspension in water, and
 c) separating the precipitate and drying.

5. A pharmaceutical composition comprising the cocrystal of claim 1 and a pharmaceutically acceptable carrier or diluent.

6. A method of treating hypercholesterolemia, hyperlipoproteinemia, or atherosclerosis, the method comprising administering an effective amount of the cocrystal of claim 1 to a subject in need thereof.

7. The cocrystal of claim 3, which is characterized by a melting peak temperature greater than 90° C. and an enthalpy of fusion greater than 40 Joule per gram when 2.5 to 4.0 mg of a sample of the cocrystal is measured in a gold sample pan hermetically sealed at a relative humidity of 25+/−10%.

8. A process for the preparation and/or purification of the cocrystal of claim 3, the process comprising:
 a) providing a solution or suspension of vanillin in water,
 b) adding Rosuvastatin calcium salt to the solution as solid or as suspension in water, and
 c) separating the precipitate and drying.

9. A pharmaceutical composition comprising the cocrystal of claim 3 and a pharmaceutically acceptable carrier or diluent.

10. A method of treating hypercholesterolemia, hyperlipoproteinemia, or atherosclerosis, the method comprising administering an effective amount of the cocrystal of claim 3 to a subject in need thereof.

* * * * *